United States Patent [19]

Sigler

[11] Patent Number: 4,709,037
[45] Date of Patent: Nov. 24, 1987

[54] BIOTINYLATING AGENTS
[75] Inventor: Gerald F. Sigler, San Diego, Calif.
[73] Assignee: Hoechst Celanese Corporation, Somerville, N.J.
[21] Appl. No.: 15,324
[22] Filed: Feb. 17, 1987
[51] Int. Cl.$^4$ ............................................. C07D 495/04
[52] U.S. Cl. ........................................ 546/271; 436/86
[58] Field of Search ........................................... 546/271

[56] References Cited

U.S. PATENT DOCUMENTS 4,149,003  4/1979  Carlsson et al. ..................... 546/261

OTHER PUBLICATIONS

Mouton, C. et al., *Arch. Biochem. Biophys.*, 218, 101 (1982).
Sutoh K. et al., *J. Mol. Biol.*, 178, 323 (1984).
Bayer E. et al., *Anal. Biochem.*, 149, 529 (1985).
Shimkus M. et al., *Proc. Natl. Acad. Sci. U.S.A.*, 82, 2593 (1985).
Herman T. et al., *Anal. Biochem.*, 156, 48 (1986).
Roseman B. et al., *Biochem. Biophys. Res. Comm.*, 137, 474 (1986).
Pierce Chemical Co., 1986–1987 Handbook, p. 305.

*Primary Examiner*—Richard A. Schwartz
*Attorney, Agent, or Firm*—Raymond R. Wittekind

[57] ABSTRACT

Compounds having a dithiopyridyl moiety linked to a biotin moiety are useful as thiol specific biotinylating agents. The biotin label can be cleaved in a reducing environment to yield the native thiol.

5 Claims, No Drawings

BIOTINYLATING AGENTS

The present invention relates to compounds that are useful as biotinylating agents. More particularly, the present invention is directed to compounds that can be used to reversibly attach biotin to low molecular weight thiols and proteins.

BACKGROUND OF THE INVENTION

Numerous reagents have been used to attach biotin to proteins via thiol and amino functions. Examples of non-cleavable biotinylating reagents specific for the thiol function include 3-(N-maleimido) propionyl biocytin, described by Bayer et al, Analytical Biochemistry, 149, 529–536 (1985), and N-iodoacetyl-N'-biotinyl-hexylenediamine described by Sutoh et al, J. Mol.Biology, 178, 323–339 (1984). Examples of cleavable biotinylating reagents specific for the amino function include 3-(4-(N-biotinoyl-6-aminocaproyloxy) phenyl) propionic acid N-hydroxysuccinimide ester (BPE) described by Mouton et al, Archives of Biochemistry and Biophysics, 218, 101–108 (1982) and sulfosuccinimidyl 2-(biotinamido) ethyl 1,3,'-dithiopropionate (NHS-SS-Biotin) sold by Pierce Chemical Company.

For some applications, it is desirable to remove the biotin residue and regenerate free, unlabeled protein. For example, the biotin residue may be employed together with immobilized avidin for the retrieval of a thiol containing protein from a mixture containing same. Once isolated, it may be important to study the protein in the unmodified state. In such cases, it is necessary to cleave the biotin residue under conditions which do not affect the integrity of the protein.

Those biotinylating reagents described above which are cleavable, i.e. BPE and NHS-SS-Biotin, leave a portion of the reagent, namely an alkylamido residue, on the protein. Since many proteins contain free thiol functions and/or disulfide functions which are readily reduced to free thiol functions, a cleavable biotinylating reagent specific for thiol functions which allows regeneration of free, unlabeled protein would have broad applicability in affinity purification techniques.

SUMMARY OF THE INVENTION

Compounds have now been synthesized and tested which can be used to reversibly attach biotin to a thiol-containing substance via a thiol-disulfide exchange reaction. Such compounds comprise a biotin moiety linked to a dithiopyridyl moiety by means of a linker arm.

In one preferred embodiment, the present invention provides the compound biotin-2-(2'-pyridyldithio)-ethylamide which has the formula:

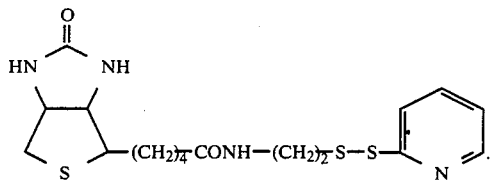

In another preferred embodiment, the present invention provides the compound N-(2-pyridyldithiopropionyl) biocytin which has the formula:

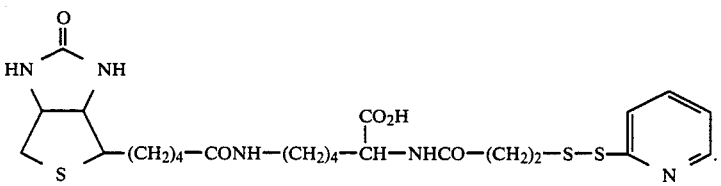

In use, the compounds of the present invention react with a thiol, such as a protein thiol, to release a pyridine-2-thione and yield a biotin-dithio-linked protein. Free protein is liberated upon reduction of the dithio group. When used in combination with immobilized avidin, the compounds of the invention afford a means for the selective isolation of proteins and protein complexes via affinity chromatography.

DETAILED DESCRIPTION OF THE INVENTION

The invention provides compounds of the formula:

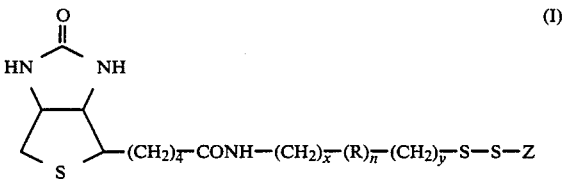

where x and y are integers of 1 to 5, n is 0 or 1, R is an acyclic linking group containing at least one amido function, and Z is a pyridyl group optionally substituted with one or more substituents of such type and in such position as to preserve the tautomerism of the thiol-thione generated upon cleavage of the —S—S— group.

The bivalent group designated R, which is defined above as an acyclic linking group containing at least one amido function, comprises a straight chain of atoms wherein the nitrogen and carbon atoms of at least one amido function are chain atoms. Preferred R groups comprise —CONH— and —CH(CO$_2$H)NHCO—.

With respect to the Z group, preferred examples include 2-pyridyl, 4-pyridyl, 5-nitro-2-pyridyl- and 5-carboxy-2-pyridyl-, however any substituent(s) which stabilizes the tautomerism of the generated thiol-thione is suitable.

Although preferred embodiments for both R and Z have been described, it should be understood that various changes and modifications as would be obvious to one having ordinary skill in this art can be made to both R and Z to create compounds which are considered as being within the scope of the invention.

Compounds of the present invention can be prepared in a number of different ways. Those methods most preferred are described below.

Compounds of formula (I) where n is 0 are prepared by contacting an acid salt of a pyridyldithioalkylamine of the formula:

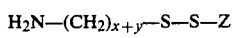
$$H_2N-(CH_2)_{x+y}-S-S-Z \quad (II)$$

where x, y and Z are as defined above, with biotin N-hydroxysuccinimide ester in the presence of a tertiary amine. The reaction is carried out in an organic solvent at a temperature of 0° to 50° C. Suitable solvents include, for example, N,N-dimethylformamide, N,N-dimethylacetamide and dimethylsulfoxide. The reaction time varies depending on the reaction temperature.

The starting compound of formula (II) can be prepared by contacting a dipyridyldisulfide of the formula:

$$Z-S-S-Z \quad (III)$$

where Z is a defined above, with an acid salt of a mercaptoalkyl amine of the formula:

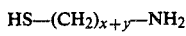
$$HS-(CH_2)_{x+y}-NH_2 \quad (IV)$$

where x and y are as defined above. The reaction is carried out in an organic solvent at a temperature of 0° to 30° C. for a period of 1 to 24 hours. Suitable solvents include ethanol, ethylacetate and dioxane.

Compounds of formula (I) where n is 1 and R is —CONH— are prepared by contacting a compound of the formula:

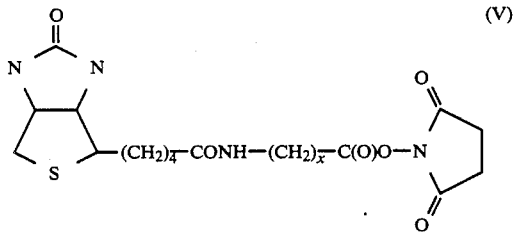

where x is as defined above, with an acid salt of a pyridyldithioalkylamine of the formula:

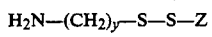
$$H_2N-(CH_2)_y-S-S-Z \quad (VI)$$

where y and Z are as defined above, in the presence of a tertiary amine. The reaction is carried out in an organic solvent at a temperature of 0° to 50° C. Suitable solvents include N,N-dimethylformamide, N,N-dimethylacetamide and dimethylsulfoxide. The reaction is carried out for from 1 to 24 hours.

Methods for the preparation of compounds of formula (V) are well known in the art. For example, preparation of the compound of formula (V) where x=5, namely preparation of biotinamido-hexanoic acid N-hydroxysuccinimide ester, is described by Costello et al., Clin. Chem., 25, 1572-1580 (1979) and is available from Behring Diagnostics, La Jolla, Calif.

Compounds of formula I where R is —CH(CO₂H)NHC(O)— can be prepared by contacting an organic acid salt of a compound of the formula:

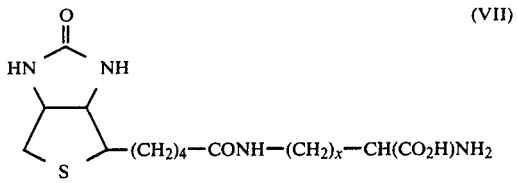

where x is as defined above, with a compound of the formula:

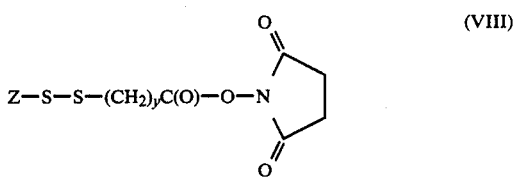

where y and Z are also as defined above. The reaction is carried out by contacting a suitable salt of (VII) dissolved in an aqueous buffer with a solution of (VIII) in a water miscible organic solvent, preferably a dipolar, aprotic solvent such as N,N-dimethylformamide. The net pH of the mixture should be such that the amino group is deprotonated and therefore reactive. A pH between 7.5 and 8.5 is optional. Suitable buffers are those that do not contain interfering functions. An alkali metal bicarbonate buffer is preferred. The reaction is carried out at a temperature range of 0° to 30° C., preferably by mixing the reagents at 0° to 5° C. and allowing the mixture to warm up to room temperature. The reactants are combined in approximately equimolar amounts at concentrations ranging between 0.1 and 0.2 M. Reaction is generally complete after 2 hours at room temperature but may be carried out longer. The product is precipitated by acidification of the mixture to a pH of 3 or less.

The starting compound of formula VII is prepared by contacting biotin N-hydroxysuccinimide ester with a compound of the formula:

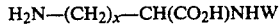
$$H_2N-(CH_2)_x-CH(CO_2H)NHW$$

where x is as defined above and W is a suitable protecting group such as tert-butyloxycarbonyl (tert—BOC). The reactants are contacted by adding a buffered solution of the protected amino acid to an organic solvent solution of the ester. This reaction is carried out at a temperature of 0° to 30° C. for a period of 1 to 24 hours. Suitable organic solvents include N,N-dimethylformamide, dimethylsulfoxide and the like. The product which is obtained is the N-α-tert-BOC derivative of VII. Prior to use, this derivative is deprotected by treatment with a suitable organic acid to obtain the acid salt derivative of VII.

Methods for the preparation of compounds of formula (VIII) are known in the art and are described in U.S. Pat. Nos. 4,149,003; 4,231,999 and 4,232,119.

The novel compounds of the present invention are cleavable, thiol specific biotinylating agents which permit regeneration of free thiol containing substance upon exposure of biotin derivatized thiol to suitable reducing conditions.

In use, compounds of the present invention react with a thiol containing substance, such as a protein thiol, to release a pyridine-2-thione and yield biotin derivatized protein. This reaction is based on thiol-disulfide exchange wherein the pyridine-2-thione released during biotinylation is a chromogen with a maximum at a wave length where most proteins are transparent ($\lambda_{max}=343$; $\epsilon_{max}=8,000$). The generation of thione permits the biotinylation to be conveniently monitored by simple spectroscopy.

Biotinylation according to the present invention comprises contacting a thiol containing substance in an aqueous buffer with a compound of formula (I) in a water-miscible organic solvent, preferably a dipolar aprotic solvent. A convenient buffer for many biochemical applications is phosphate buffered saline (PBS) with a pH of 7.4; however, a variety of buffers in the pH range of 6 to 9 are satisfactory with the exact composition usually being a function of the molecule to be labeled. In the preferred mode, the buffer also contains a small amount of an antioxidant for thiol groups. An example of a suitable antioxidant is ethylenediaminetetraacetic acid (EDTA). The biotinylating reaction, which is a thiol-disulfide exchange, is carried out at a temperature range of 4° to 30° C. for a period of 1 to 8 hours. As mentioned above, the progress of the reaction is conveniently monitored by spectrophotometry, since the byproduct of condensation is a chromogen. Once the reaction is judged to complete, the excess biotinylating agent plus byproduct are removed. In the case of macromolecules, this is easily accomplished by gel filtration or dialysis.

The compounds of the present invention can be used to biotinylate various substances via native or artifically induced thiol groups. Such substances comprise proteins such as, for example, hormones, enzymes and antibodies as well as low molecular weight substances.

Use of the compounds of formula (I) in combination with appropriate avidin conjugates, particularly enzyme labeled avidin conjugates, provides a universal multipurpose thiol specific probe. For example, direct staining of blotted thiol protein with a compound of formula (I) enables subsequent detection with an avidin enzyme complex.

Use of the compounds of formula (I) in combination with an avidin affinity matrix (i.e., immobilized avidin) provides a means for the selective isolation of proteins and protein complexes via affinity chromatography. For example, antibody, having an affinity for a particular target antigen and biotinylated with a compound of formula (I) is added to crude mixture containing the target antigen. The target antigen binds to the biotin labeled antibody and the resulting complex is recovered by means of an avidin affinity matrix. The bound complex can be recovered from the avidin matrix by reduction of the disulfide bond with a suitable thiol such as dithiothreitol.

Compounds of the present invention are particularly suited for attaching biotin to an antibody or fragment thereof. Antigen binding sites of an antibody contain free amino groups. If an antibody is labeled with a biotin labeling agent which is reactive with these amino functions, the ability of the labeled antibody to bind its antigen is disturbed. If however an antibody is subjected to mild reduction in order to convert some of the intrachain and/or interchain disulfide groups to free thiol groups, the antibody may be subsequently labeled with biotin by means of the thiol specific compounds of the present invention. By utilizing a thiol specific labeling agent, one avoids interfering with the antigen binding sites.

The invention will now be illustrated by way of specific examples.

EXAMPLE I

A solution of 2,2,'-dipyridyldisulfide is prepared by dissolving 2.64 g (12 mmol) of the disulfide in 75 ml of reagent ethanol. A filtered solution of 1.29 g (11.3 mmol) of 2-mercaptoethylamine hydrochloride in 75 ml reagent ethanol is then added with stirring to the first solution over a period of one hour. After the addition is complete, stirring is continued at room temperature. After two hours, the reaction mixture is placed in the refrigerator for 18 hours. Thereafter the resulting suspension is filtered to remove insoluble material, namely, oxidized 2-mercaptoethylamine, and the filtrate is diluted to 500 ml with diethylether. The precipitate which forms is removed by filtration and the filtrate is rotary evaporated to a volume of 50 ml. The concentrated filtrate is diluted again to 500 ml with diethyl ether whereby a flocculent precipitate forms. After cooling to 4° C., the product is recovered and dried under vacuum to yield 2-(2,'-pyridyldithio)-ethylamine hydrochloride.

The product is nearly homogeneous by TLC (system=n-butanol: acetic acid: water (4:1:1); Merck silica gel 60 F-254 plates) showing a UV absorbing, ninhydrin positive spot at $R_f 0.45$. NMR in $D_2O$ is consistent with the assigned structure.

EXAMPLE II

A solution of biotin N-hydroxysuccinimide ester and 2-(2,'-pyridyldithio)-ethylamine hydrochloride is prepared by dissolving 0.73 g (2.15 mmol) of ester and 0.53 g (2.39 mmol) of amine hydrochloride in 15 ml N,N-dimethylformamide. Triethylamine (0.63 ml, 4.54 mmol) is added and the mixture is covered and stirred at room temperature for 18 hours. The reaction mixture is then filtered to remove triethylamine hydrochloride precipitate and the filtrate is rotary evaporated under vacuum at 50° C. The oil which is obtained is triturated with 25 ml of distilled water to produce a flocculent solid which is collected, dried and recrystallized from methanol (25 ml)/water (100 ml). The recrystallized solid is dried under vacuum in the presence of $P_2O_5$ to yield 0.37 g of biotin-2-(2,'-pyridyldithio)-ethylamine.

Analysis of the product by TLC (system=n-butanol:acetic acid: water (4:1:1); Merck silica gel 60 F-254 plates) shows a major UV absorbing, iodine staining spot at $R_f 0.65$. NMR in DMSO-$D_6$ shows characteristic peaks for pyridylthio and biotin moieties. Treatment of the product with excess of 2-mercaptoethylamine results in almost stoichiometric release of 2-pyridylthione as measured by spectral assay ($A_{max}=343$ nm; $\epsilon_{max}=7.06\times10^4$).

EXAMPLE III

Lyophilized *Escherichia coli* β-galactosidase (Behring Diagnostics, EIA grade having an average of 14 free sulfhydryl groups per molecule) is dissolved in pH 7.4 phosphate buffered saline containing 1 mM ethylenediaminetetraacetic acid to give 4.0 ml of stock solution having a net enzyme concentration of 0.7 mg/ml and a total solids concentration of 3.1 mg/ml. One-half of the stock solution (1.4 mg or 3.0 nmol enzyme based on a molecular weight of 465,000) is added to a 4 ml quartz cuvette. The remainder of the stock solution is added to a second matched cuvette and the cuvettes are zeroed against each other at 343 nm in a Hitachi 100-80 model spectrophotometer.

A 4 0 mM solution of biotin-2-(2,'-pyridyldithio) ethylamide in N,N-dimethylformamide is prepared by adding 8.34 mg of the biotin derivative to 5 ml of DMF. Using a syringe, 39 μl (156 mmol) of biotin reagent is added to one of the cuvettes containing 2 ml of β-galactosidase solution. Mixing of the two solutions is immediately effected. To the other cuvette, also containing 2 ml of β-galactosidase solution, is added 39 μl of solvent. Mixing of these solutions is also effected immediately.

The filled cuvettes are positioned in the spectrophotometer and the absorbance due to release of 2-pyridylthione is monitored continuously at 343 nm. After 1.5 hours, an absorbance of 0.161 is realized which corresponds to 45.6 nmol of 2-pyridylthione. Based on the stoichiometry of the reaction, the yield of 2-pyridylthione corresponds to an average of 15 nmol of biotin reacted per nmol of enzyme.

Excess biotin reagent is removed from the biotinylated enzyme by passing the reaction solution through a Sephadex G-25 column (Pharmacia PD-10) equilibrated with pH 7.4 buffer. The fractions containing biotinylated enzyme are located by A280 protein absorbance and pooled to yield 3.4 ml of solution.

EXAMPLE IV

One ml of the biotinylated enzyme solution from EXAMPLE III which solution contains 0.70 protein absorbance units at 280 nm, is allowed to percolate through a bed of 1 ml avidin-agarose gel (Behring Diagnostics, La Jolla, Calif.). After the effluent is collected, the bed is washed with 1.7 ml of pH 7.4 buffer. The combined effluents are found to contain only 0.04 protein absorbance units at 280 nm which indicates that 94% of the biotinylated enzyme is retained on the column. In a control experiment, virtually all of the absorbance units generated by a non-biotinylated β-galactosidase sample appear in the effluent indicating that the unmodified enzyme is not retained on the column.

EXAMPLE V

One ml of the immobilized biotinylated β-galactosidase product prepared as described in EXAMPLE IV is treated with 4 ml of a 50 mM solution of dithiothreitol in pH 7.4 phosphate buffered saline containing 1 mM ethylenediamine tetraacetic acid. The dithiothreitol reagent is filtered through the gel bed at room temperature and the filtrate collected. During this process the gel is exposed to the reagent for a period of approximately 2 hours. Total collected filtrate is passed through a gel filtration column of Sephadex G-25 to separate dithiothreitol from recovered β-galactosidase. Of a total of 1.57 $OD_{280}$ units of biotin labeled β-galactosidase bound to the avidin-agarose gel, 1.28 $OD_{280}$ units are recovered, indicating that 82% of the enzyme is cleaved.

EXAMPLE VI

Biotin N-hydroxysuccinimide ester (1.10 g, 3.23 mmol) is dissolved in 11 ml N,N-dimethylformamide and the resulting solution is cooled to 5° C. in an ice bath. Thereafter, a solution of 0.927 g (3.77 mmol) of N-α-t-BOC-L-lysine in 11 ml 1M sodium bicarbonate is added, with stirring, to the first solution over a period of 1.5 hours. Stirring is continued overnight at room temperature. The reaction mixture is then vacuum filtered and the filtrate rotary evaporated under reduced pressure at 35° C. The white cloudy oil which is obtained is dissolved in 27 ml of water and the resulting solution cooled to 5° C. in an ice bath. When the solution is acidified to pH3 with 1 N hydrochloric acid, a white precipitate forms. The reaction mixture is then stirred for approximately 30 minutes and then vacuum filtered. The white solid which is obtained is washed with ice-cold water and then dried under vacuum overnight at 40° C. in the presence of $P_2O_5$ to yield 1.10 g of N-α-t-BOC-biocytin.

EXAMPLE VII

A mixture of 4.5 ml trifluoroacetic acid and 0.50 ml anisole is added to 1.08 g (2.29 mmol) of N-α-t-BOC-biocytin. The resulting reaction mixture is stirred at room temperature for approximately 30 minutes and then rotary evaporated under vacuum at 30° C. to obtain a thick yellow oil. The oil is triturated with 20 ml of ethyl ether and the resulting suspension vacuum filtered. The white solid which is obtained is dried overnight under vacuum in the presence of sodium hydroxide to yield 1.34 g of biocytin trifluoroacetate.

EXAMPLE VIII

Biocytin trifluoroacetate (0.50 g, 1.03 mmol) is dissolved in 5.0 ml of 0.5 M sodium bicarbonate buffer, pH8.3, and the resulting solution is then cooled to 5° C. in an ice bath. Thereafter, a solution of 0.32 g (1.03 mmol) of N-succinimidyl 3-(2-pyridyldithio)-propionate in 2 ml N,N-dimethylformamide is added dropwise with stirring to the first solution. After the addition is complete, stirring is continued and the reaction is allowed to come to room temperature. After two hours, the reaction mixture is acidified to pH3 with 1 N hydrochloric acid and placed in the refrigerator overnight to precipitate the product. The suspension which results on cooling is vacuum filtered and the recovered solid dried under vacuum to yield 0.36 g of N-(2-pyridyldithio propionyl) biocytin having a melting point of 166°-169° C.

The product is nearly homogeneous by TLC (system=n-propanol:water (7:3); Merck silica gel 60 F-254 plates) showing a single UV absorbing, iodine staining component. Upon treatment of the product with excess 2-mercaptoethylamine, more than 90% of the pyridyldithio moiety is released as measured by spectral assay ($A_{max}$=343 nm; $e_{max}$=7.06×$10^4$). NMR in DMSO - $D_6$ shows characteristic peaks for the pyridylthio and biotinyl moieties.

EXAMPLE IX

Using the method of EXAMPLE III but replacing biotin-2-(2'-pyridyldithio)-ethylamide with N-(2-pyridyl dithiopropionyl)-biocytin yields β-galactosidase enzyme biotinylated with the latter reagent. The measured absorbance of the reaction, which is due to release of 2-pyridylthione, corresponds to an average of 12 nmol of 2-pyridylthione released per nmol of enzyme treated.

Excess biotin reagent is removed from the biotinylated enzyme by passing the reaction solution through a Sephadex G-25 column equilibrated with pH 7.4 phosphate buffered saline containing 1 mM ethylenediamine tetraacetic acid. The fractions containing biotinylated enzyme are located by $A_{280}$ protein absorbance and pooled.

EXAMPLE X

Biotinylated enzyme solution obtained in EXAMPLE IX is treated according to the procedure described in EXAMPLE IV to obtain biotinylated β-galactosidase immobilized on avidin agarose.

Of a total of 3.00 $OD_{280}$ units of biotin labeled β-galactosidase added to the avidin-agarose gel, 2.60 $OD_{280}$ units are bound, indicating that 86% of the biotinylated enzyme is retained on the column.

EXAMPLE XI

The immobilized biotin labeled β-galactosidase produce of EXAMPLE X is treated according to the procedure of EXAMPLE V to obtain unlabeled β-galactosidase.

Of a total of 2.60 $OD_{280}$ units of enzyme bound to the avidin-agarose gel, 1.84 $OD_{280}$ units were recovered indicating that 71% of the enzyme is cleaved from the column.

What is claimed is:

1. A compound of the formula:

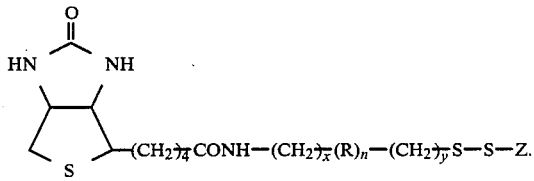

where x and y are integers of 1 to 5, n is 0 or 1, R is —CONH— or —CN($CO_2$H)NHCO— and Z is a pyridyl group optionally substituted with one or more substituents of such type and in such position as to preserve the tautomerism of the thiolthione generated upon cleavage of the —S—S— group.

2. A compound according to claim 1 where Z is selected from the group consisting of 2-pyridyl, 4-pyridyl, 5-nitro-2-pyridyl and 5-carboxy-2-pyridyl.

3. A compound according to claim 2 wherein Z is 2-pyridyl or 4-pyridyl.

4. The compound of claim 3: biotin-2-(2'-pyridyldithio)-ethylamide having the formula:

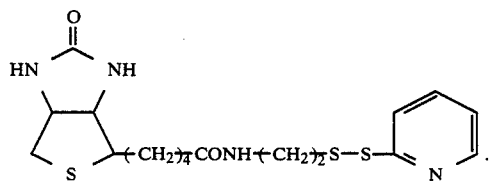

5. The compound of claim 3: N-(2-pyridyldithiopropionyl) biocytin having the formula:

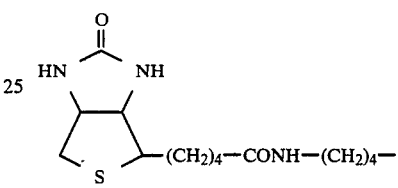
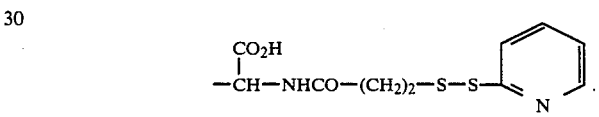

* * * * *

UNITED STATES PATENT AND TRADEMARK OFFICE
CERTIFICATE OF CORRECTION

PATENT NO. : 4,709,037

DATED : November 24, 1987

INVENTOR(S) : Gerald F. Sigler

It is certified that error appears in the above-identified patent and that said Letters Patent is hereby corrected as shown below:

Column 9, line 33: "-CN($CO_2$H)NHCO- should be -- -CH($CO_2$H)NHCO --

Signed and Sealed this

Twentieth Day of September, 1988

Attest:

DONALD J. QUIGG

Attesting Officer

Commissioner of Patents and Trademarks